(12) United States Patent
Kahn et al.

(10) Patent No.: US 9,875,337 B2
(45) Date of Patent: Jan. 23, 2018

(54) METHOD AND APPARATUS TO PRESENT A VIRTUAL USER

(71) Applicant: DP Technologies, Inc., Scotts Valley, CA (US)

(72) Inventors: Philippe Kahn, Aptos, CA (US); Arthur Kinsolving, Santa Cruz, CA (US)

(73) Assignee: DP TECHNOLOGIES, INC., Scotts Valley, CA (US)

( * ) Notice: Subject to any disclaimer, the term of this patent is extended or adjusted under 35 U.S.C. 154(b) by 104 days.

(21) Appl. No.: 14/229,815

(22) Filed: Mar. 28, 2014

(65) Prior Publication Data

US 2014/0214454 A1   Jul. 31, 2014

Related U.S. Application Data

(63) Continuation of application No. 11/682,218, filed on Mar. 5, 2007, now Pat. No. 8,725,527.

(60) Provisional application No. 60/778,862, filed on Mar. 3, 2006.

(51) Int. Cl.
*G06F 19/00* (2011.01)
*G06Q 50/22* (2012.01)

(52) U.S. Cl.
CPC .......... *G06F 19/322* (2013.01); *G06Q 50/22* (2013.01)

(58) Field of Classification Search
None
See application file for complete search history.

(56) References Cited

U.S. PATENT DOCUMENTS

| | | |
|---|---|---|
| 5,331,549 A | 7/1994 | Crawford, Jr. |
| 5,737,439 A | 4/1998 | Lapsley et al. |
| 5,771,001 A | 6/1998 | Cobb |
| 5,885,609 A | 3/1999 | Knapp |
| 5,960,085 A | 9/1999 | de la Huerga |
| 5,976,083 A | 11/1999 | Richardson et al. |
| 5,989,200 A | 11/1999 | Yoshimura et al. |
| 6,132,337 A | 10/2000 | Krupka et al. |
| 6,241,684 B1 | 6/2001 | Amano et al. |
| 6,408,330 B1 | 6/2002 | de la Huerga |
| 6,493,652 B1 | 12/2002 | Ohlenbusch et al. |
| 6,522,266 B1 | 2/2003 | Soehren et al. |
| 6,595,929 B2 | 7/2003 | Stivoric et al. |
| 6,786,866 B2 | 9/2004 | Odagiri et al. |
| 6,788,980 B1 | 9/2004 | Johnson |
| 6,813,582 B2 | 11/2004 | Levi et al. |
| 6,898,550 B1 | 5/2005 | Blackadar et al. |
| 6,980,958 B1 * | 12/2005 | Surwit ................ G06F 19/3406 600/301 |
| 6,990,660 B2 | 1/2006 | Moshir et al. |

(Continued)

FOREIGN PATENT DOCUMENTS

| | | |
|---|---|---|
| JP | 11347021 A | 12/1999 |
| JP | 2004-145875 A | 5/2004 |

(Continued)

OTHER PUBLICATIONS

Non-Final Office Action for U.S. Appl. No. 14/256,918, dated Sep. 11, 2015, 17 pages.

*Primary Examiner* — Valerie Lubin
(74) *Attorney, Agent, or Firm* — Nicholson De Vos Webster & Elliott LLP

(57) ABSTRACT

A method and apparatus for providing an interactive interface to user health data is described.

14 Claims, 11 Drawing Sheets

(56) References Cited

U.S. PATENT DOCUMENTS

| | | |
|---|---|---|
| 7,009,511 B2 | 3/2006 | Mazar et al. |
| 7,043,752 B2 | 5/2006 | Royer |
| 7,120,830 B2 | 10/2006 | Tonack |
| 7,155,507 B2 | 12/2006 | Hirano et al. |
| 7,353,179 B2 | 4/2008 | Ott |
| 7,379,999 B1 | 5/2008 | Zhou et al. |
| 7,457,872 B2 | 11/2008 | Aton et al. |
| 7,561,960 B2 | 7/2009 | Soehren |
| 7,664,657 B1 | 2/2010 | Letzt et al. |
| 2001/0053984 A1 | 12/2001 | Joyce et al. |
| 2001/0056359 A1 | 12/2001 | Abreu |
| 2002/0016719 A1 | 2/2002 | Nemeth et al. |
| 2002/0028988 A1 | 3/2002 | Suzuki et al. |
| 2002/0138017 A1 | 9/2002 | Bui et al. |
| 2003/0101260 A1 | 5/2003 | Dacier et al. |
| 2003/0139908 A1 | 7/2003 | Wegerich et al. |
| 2003/0149526 A1 | 8/2003 | Zhou et al. |
| 2003/0191608 A1 | 10/2003 | Anderson et al. |
| 2003/0196141 A1 | 10/2003 | Shaw |
| 2003/0208113 A1 | 11/2003 | Mault et al. |
| 2003/0227487 A1 | 12/2003 | Hugh |
| 2003/0233257 A1* | 12/2003 | Matian ............... G06F 19/322 705/3 |
| 2003/0236625 A1 | 12/2003 | Brown et al. |
| 2004/0017300 A1 | 1/2004 | Kotzin et al. |
| 2004/0024846 A1 | 2/2004 | Randall et al. |
| 2004/0043760 A1 | 3/2004 | Rosenfeld et al. |
| 2004/0044493 A1 | 3/2004 | Coulthard |
| 2004/0078219 A1 | 4/2004 | Kaylor et al. |
| 2004/0078220 A1 | 4/2004 | Jackson |
| 2004/0117204 A1 | 6/2004 | Mazar et al. |
| 2004/0122294 A1 | 6/2004 | Hatlestad et al. |
| 2004/0122295 A1 | 6/2004 | Hatlestad et al. |
| 2004/0122296 A1 | 6/2004 | Hatlestad et al. |
| 2004/0122297 A1 | 6/2004 | Stahmann et al. |
| 2004/0122333 A1 | 6/2004 | Nissila |
| 2004/0122484 A1 | 6/2004 | Hatlestad et al. |
| 2004/0122485 A1 | 6/2004 | Stahmann et al. |
| 2004/0122486 A1 | 6/2004 | Stahmann et al. |
| 2004/0122487 A1 | 6/2004 | Hatlestad et al. |
| 2004/0146048 A1 | 7/2004 | Cotte |
| 2004/0148340 A1 | 7/2004 | Cotte |
| 2004/0148341 A1 | 7/2004 | Cotte |
| 2004/0148342 A1 | 7/2004 | Cotte |
| 2004/0148351 A1 | 7/2004 | Cotte |
| 2004/0148392 A1 | 7/2004 | Cotte |
| 2004/0215755 A1 | 10/2004 | O'Neill |
| 2004/0247748 A1 | 12/2004 | Bronkema |
| 2004/0259494 A1 | 12/2004 | Mazar |
| 2004/0267573 A1 | 12/2004 | Federico |
| 2005/0027567 A1 | 2/2005 | Taha |
| 2005/0033200 A1 | 2/2005 | Soehren et al. |
| 2005/0038691 A1 | 2/2005 | Babu |
| 2005/0039127 A1 | 2/2005 | Davis |
| 2005/0054938 A1 | 3/2005 | Wehman et al. |
| 2005/0079873 A1 | 4/2005 | Caspi et al. |
| 2005/0101841 A9 | 5/2005 | Kaylor et al. |
| 2005/0102167 A1 | 5/2005 | Kapoor |
| 2005/0107944 A1 | 5/2005 | Hovestadt et al. |
| 2005/0113650 A1 | 5/2005 | Pacione et al. |
| 2005/0114502 A1 | 5/2005 | Raden et al. |
| 2005/0131480 A1 | 6/2005 | Kramer |
| 2005/0131736 A1 | 6/2005 | Nelson et al. |
| 2005/0146431 A1 | 7/2005 | Hastings et al. |
| 2005/0177051 A1* | 8/2005 | Almen ............... A61B 5/02405 600/509 |
| 2005/0182824 A1 | 8/2005 | Cotte |
| 2005/0235058 A1 | 10/2005 | Rackus et al. |
| 2005/0256414 A1 | 11/2005 | Kettunen et al. |
| 2005/0262237 A1 | 11/2005 | Fulton et al. |
| 2005/0272564 A1 | 12/2005 | Pyles et al. |
| 2006/0020177 A1 | 1/2006 | Seo et al. |
| 2006/0064020 A1* | 3/2006 | Burnes ............... A61B 5/002 600/481 |
| 2006/0064276 A1 | 3/2006 | Ren et al. |
| 2006/0109113 A1 | 5/2006 | Reyes et al. |
| 2006/0154642 A1 | 7/2006 | Scannell, Jr. |
| 2006/0161459 A1 | 7/2006 | Rosenfeld et al. |
| 2006/0206587 A1 | 9/2006 | Fabbrocino |
| 2006/0249683 A1 | 11/2006 | Goldberg et al. |
| 2007/0017136 A1 | 1/2007 | Mosher et al. |
| 2007/0024441 A1 | 2/2007 | Kahn et al. |
| 2007/0050157 A1 | 3/2007 | Kahn et al. |
| 2007/0067725 A1 | 3/2007 | Cahill et al. |
| 2007/0073934 A1 | 3/2007 | Rogers |
| 2007/0192483 A1 | 8/2007 | Rezvani et al. |
| 2007/0239399 A1 | 10/2007 | Shyenblat et al. |
| 2007/0260418 A1 | 11/2007 | Ladetto et al. |
| 2008/0254944 A1 | 10/2008 | Muri et al. |
| 2009/0099668 A1 | 4/2009 | Lehman et al. |

FOREIGN PATENT DOCUMENTS

| | | |
|---|---|---|
| JP | 2004-174168 A | 6/2004 |
| WO | WO 02/088926 A1 | 11/2002 |

* cited by examiner

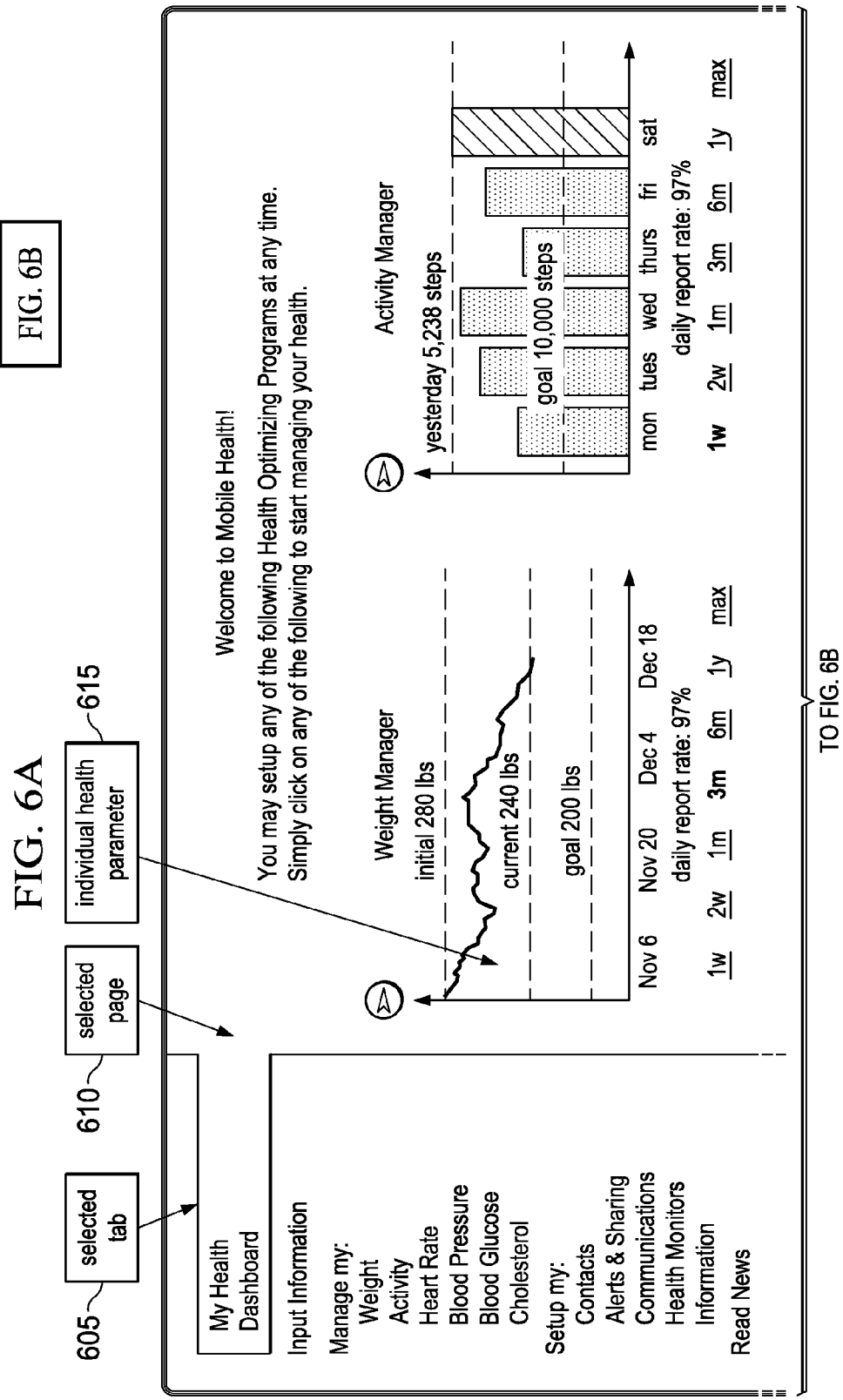

METHOD AND APPARATUS TO PRESENT A VIRTUAL USER

RELATED CASES

This application is a continuation of application Ser. No. 11/682,218, filed Mar. 5, 2007, which claims priority to U.S. Provisional Patent Application Ser. No. 60/778,862, filed Mar. 3, 2006.

FIELD OF THE INVENTION

The present invention relates to user data presentation, and more particularly to interfaces for interacting with health data.

BACKGROUND

Electrical sensors, monitors, and devices built by an ever-changing group of manufacturers are constantly entering the market. Collectively, these devices will be referred to as SMDs (sensors, monitors, devices).

Users are increasingly looking to bring access to all of these SMDs to their daily routine. In the prior art, this remote access has been limited to historical information access such as databases or e-mails, while other SMD data is not remotely accessible.

In the prior art, SMDs functioned as individual devices, and collecting and accessing such data was difficult.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

The method and apparatus described is a user interface to enable a user to interact with, and enter data into, an SMD Integration and Management Server (SIMS). The SIMS system offers a continuous always-on connection to the SMD data. The virtual user is a conceptual framework for viewing the comprehensive data available about a user on the SIMS. Virtual user can represent a single user (for example a user examining his or her own data), a platform for displaying health data from multiple users (for example for a family), or a platform for displaying health data to healthcare providers, in a context that enables them to easily determine when one or more of their patients may need attention. By presenting a virtual user, the viewer can become more pro-active about handling various issues. Furthermore, the virtual user enables the simple presentation of overall health status, showing the interaction between various individual health measurements.

Figure 1:
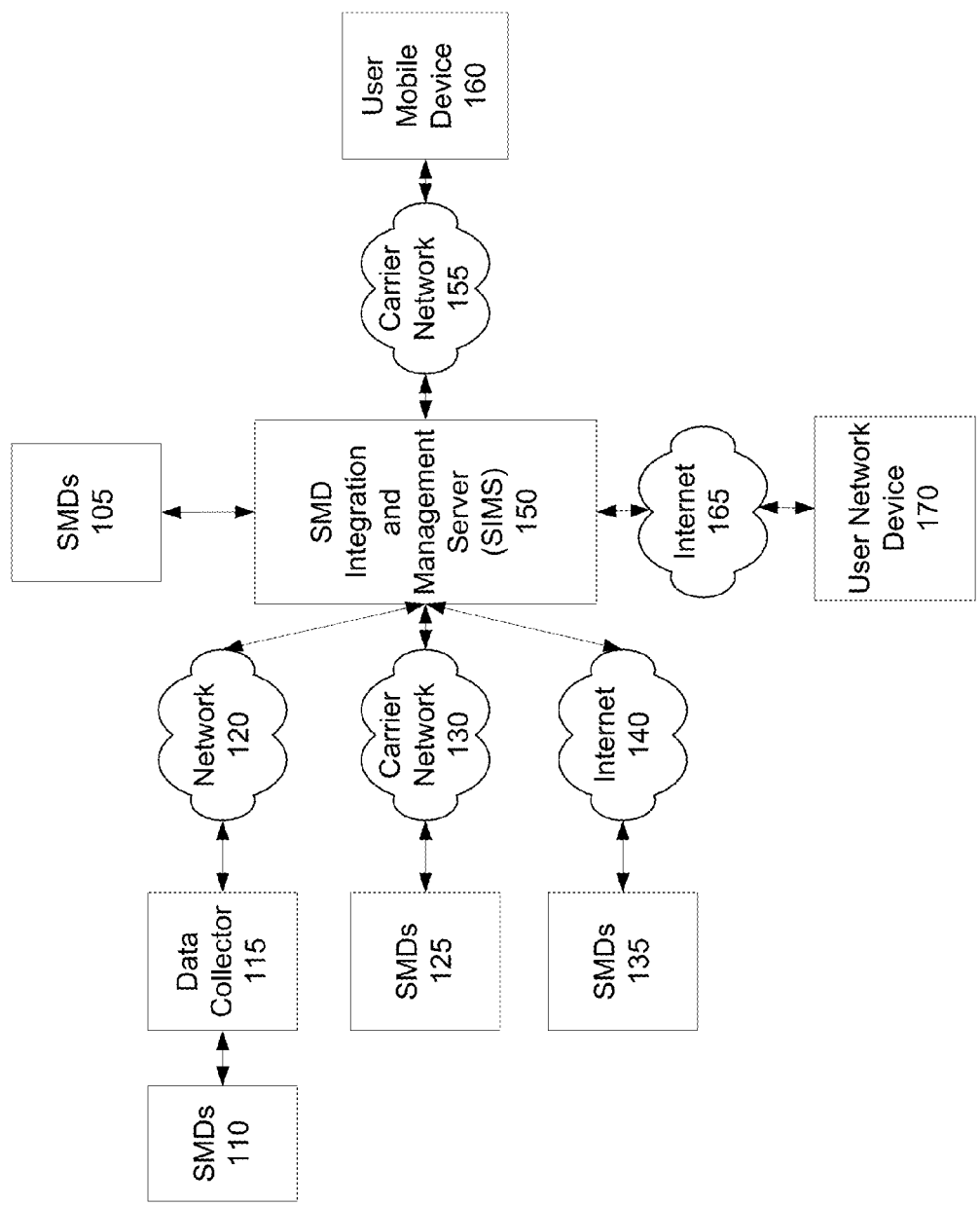
FIG. 1 is a block diagram of one embodiment of a network diagram including an SMD Integration and Management Server (SIMS).

FIG. 1 is a network diagram of one embodiment of the various elements of the system. The various SMDs 110 are coupled through various means to the SMD Integration and Management Server (SIMS) 150. They may be coupled directly, coupled through carrier network 130, coupled through the Internet 140, or they may be coupled through a data collector 115, which accumulates data from sensor 110, and sends it through network 120, 130, or 140 to SIMS 150. In another embodiment, SMDs may be independent devices which are not coupled to the SIMS 150. Rather, the SIMS 150 may receive data from a user 170 via a network 165. The network may be the Internet 140, a carrier network 130, or any other network. In one embodiment, the SIMS 150 includes a web server, which enables the user to access certain user interface pages, to enter, read, share, and otherwise interact with the collected data.

The data accumulated by SIMS 150 may be available to the user via a user mobile device 160, which accesses SIMS 150 through carrier network 155 or another network, or via another user device 170, such as a computer.

Figure 2:
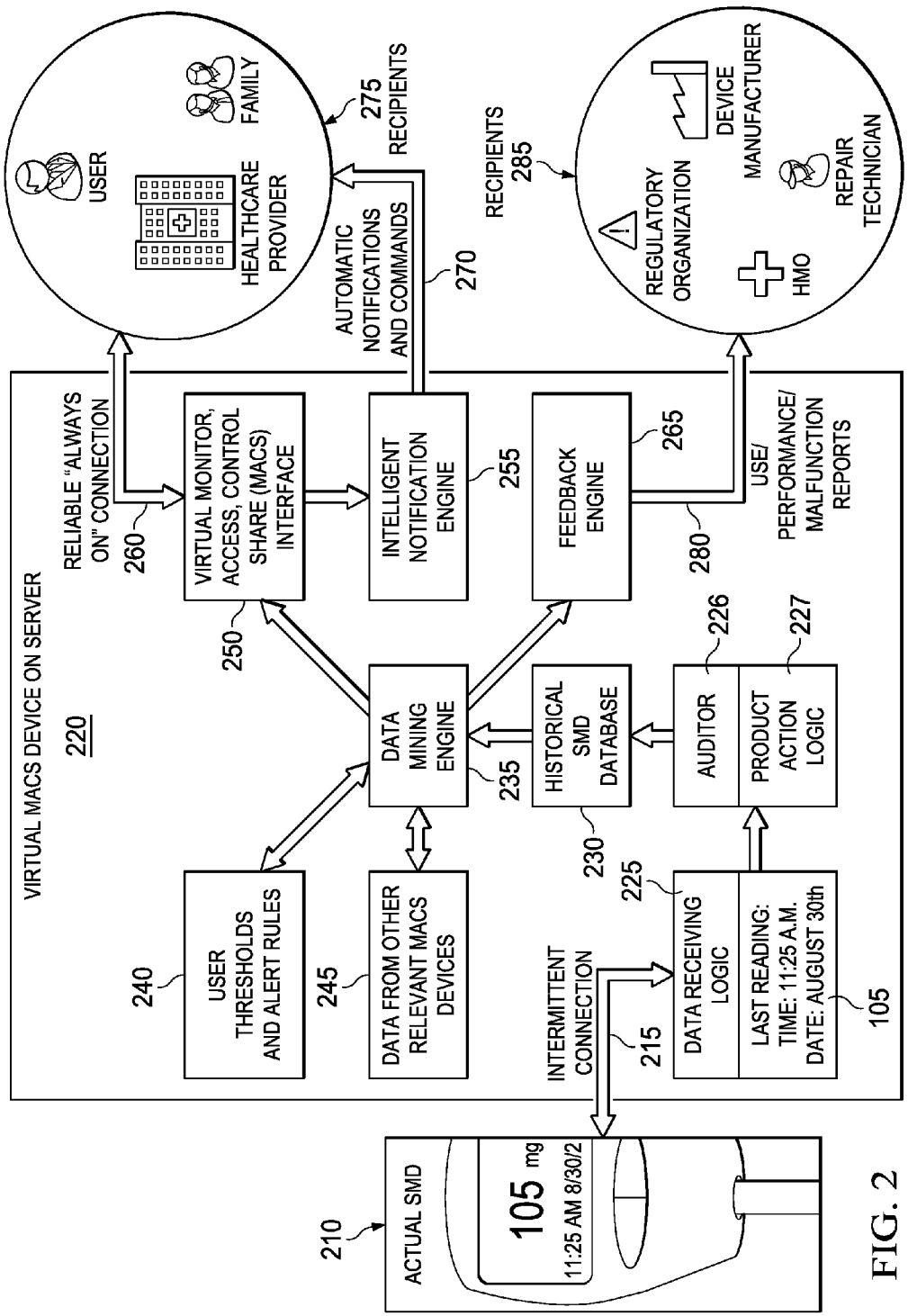
FIG. 2 is a block diagram of a virtual MACS device on the SIMS.

FIG. 2 is a block diagram illustrating one embodiment of a Virtual Management, Access, Control, Share (MACS) device on the SIMS server and its relationship to the actual SMD. The actual SMD 210 has an intermittent connection 215 to a server 220. The connection 215 may be through the Internet, through a carrier network, or through other means. The server 220 may be located in the same location as the real SMD 210.

The data receiving logic 225 receives the data from the actual SMD 210 or the user via an intermittent connection 215. The data is stored in historical database 230. The historical data is used by data mining engine 235, to present virtual MACS device 250 via a reliable always-on connection 260 to various recipients 275. In a healthcare setting for example, the recipients may include the user, healthcare providers, and family.

In one embodiment, data mining engine 235 may further interface with user alerts and rules 240 to generate notifications through intelligent notification engine 255. Intelligent notification engine 255 can send automatic notifications to designated recipients 275, when certain threshold or alert conditions are met. The threshold or alert conditions may include historical data, trend analysis, variance from charted trends, simple threshold, or any combination of the use of historical and current data from the actual SMD 210, or combination of SMDs. In one embodiment, the data mining engine 235 constantly monitors the database 230, to ensure that the alert rules and user thresholds 240 have not been triggered. Intelligent notification engine 255 can, in one embodiment, trigger a notification in an appropriate format to any designated recipient.

In one embodiment, in addition to the database 230, data from other relevant actual SMDs may be received as well via logic 245. For example, in health setting, in addition to the glucose meter, exercise data, medical reports, and/or other relevant conditions may be monitored. The threshold and alert rules 240 may utilize a combination of data from more than one real SMD to trigger a notification or command 270.

Figure 3:
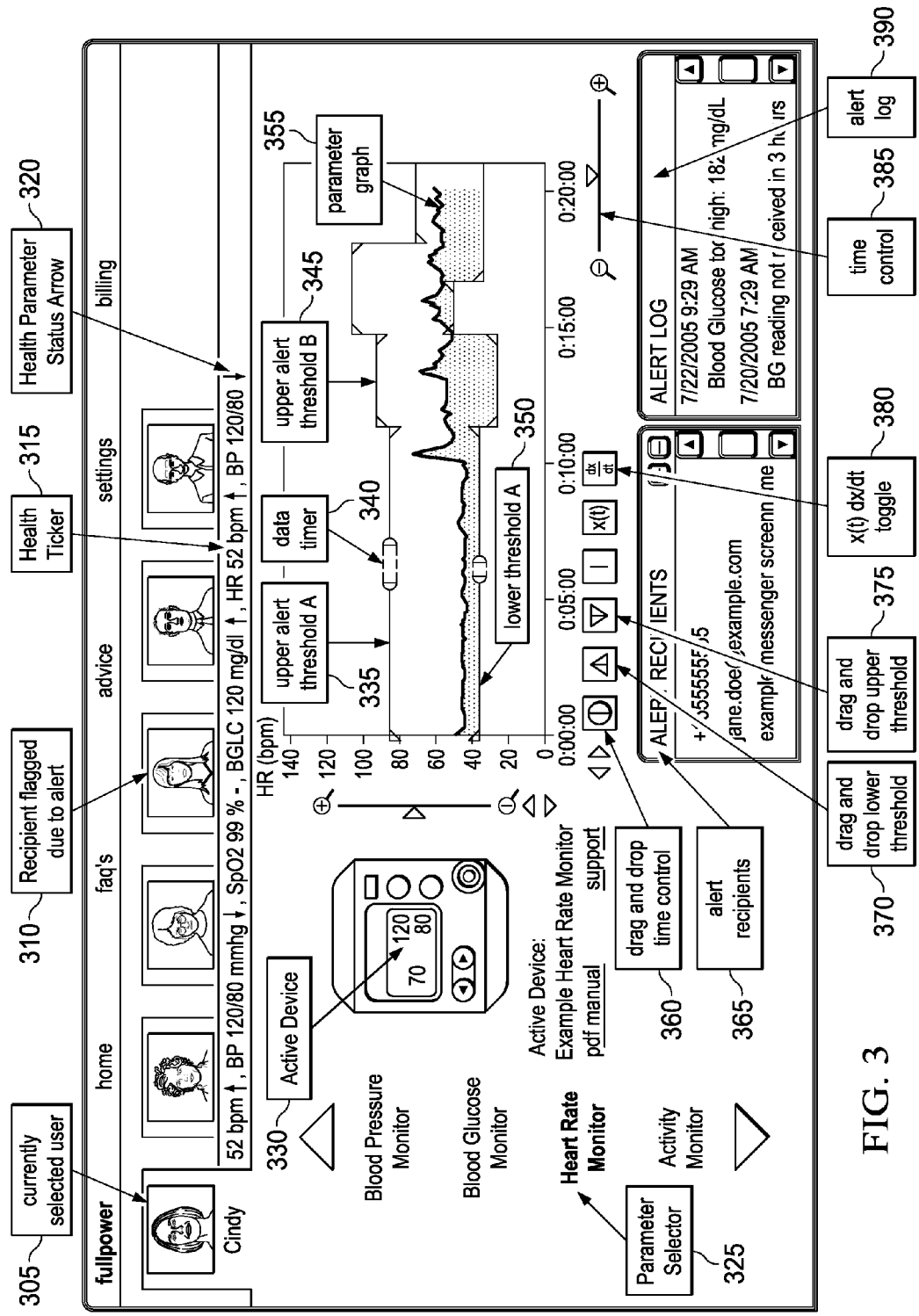
FIG. 3 is an exemplary health display for a group of users.

FIG. 3 is an exemplary health display for a family or other group of users. In one embodiment, each person in the family, or other group of users whose data is displayed in this format, has a picture, name, or other identifier. In one embodiment, if one of the user's health parameter values are outside acceptable parameters, or meet one or more alert triggers, that user's identifier is flagged 310 to visually indicate the problem. In one embodiment, a separate alert may also be sent to designated destinations. One embodiment of the alert mechanism is described in more detail in co-pending U.S. application Ser. No. 11/192,549, which is incorporated herein by reference.

In one embodiment, the family or other group health display may also include a health ticker 315, which includes heath data from each of the users within the display. In one embodiment, the health ticker utilizes color, font, images, icons, or other indicators to identify the user associated with each item on the ticker. In one embodiment, the system also uses color coding to flag any items that may be problematic (i.e. a significant increase in blood pressure, a significant drop in blood oxygen levels, negative trends, or other problems). Alternative means of tagging to highlight items that may be problematic, or indicate bad trends, may be used. In one embodiment, the user's icon/image or other indicator is concurrently highlighted or flagged, as shown in 310.

In one embodiment, the health display also enables a user to select a particular user 305, and/or a particular health parameter 325, to obtain additional information.

In one embodiment, the health parameter information may include identification of the SMD(s) 330 associated with the health parameter, as well as a graph 355 showing the health parameter's changes over time. In one embodiment, in addition to the changes over time, the display may include trend lines.

In one embodiment, the user can change the alert settings using a graphical interface. In one embodiment, the graphical interface overlays the actual data. One example of this is shown in FIG. 3. In the example in FIG. 3, when the user is adjusting the upper or lower thresholds 335, 345, 350 he or she can visually see how those thresholds relate to the actual historical health data. In one embodiment, the user may set multiple thresholds 335, 345, associated with different time units. For example, the blood glucose levels are generally different first thing in the morning, and in the early afternoon. Therefore, time-based thresholds 335, 345 may be set. By allowing the user to immediately see how these alert levels relate to their own historical data. This ensures, for example, that a user will not set a threshold which has historically been crossed without any health implications.

In one embodiment, the user may also set a data timer 340, which sets a period within which a measurement is expected (i.e. asking the user to measure their blood pressure every three hours at a minimum). The data timer 340, in one embodiment sends an alert or other notification if data is not received within the prescribed period of time. In one embodiment, for example, the "glucose testing" window may be between 11 a.m. and 2 p.m. to receive a post-lunch measurement. If no data is received within that window, an alert may be sent to the user, reminding them to eat lunch and/or take a measurement.

In one embodiment, each type of control, time control 360, lower threshold 370, upper threshold 375, change over time (x(t)) and acceleration (dx/dt) 380, may be controlled using drag and drop controls. Alternative methods of controlling these settings may be implemented.

Each of these thresholds may have one or more alerts associated with them. The alerts may be controlled from the health display using alert recipients list 365. In one embodiment, the alert recipients are controlled by a user. In another embodiment, the recipient's list 365 may be controlled by a parent, doctor, or other authorized individual or group.

In one embodiment, an alert log 390 provides a historical view of past alerts that were sent. In one embodiment, the alert log also includes who the alert was sent to. In one embodiment, each alert record in the alert log 390 may also include the resolution. For example, an alert log entry may read:

Blood Glucose Reading not received in 3 hours, email to John

Blood Glucose Reading not received in 4 hours, phone call to John, email to Cindy Blood Glucose Reading received, alert cleared.

In one embodiment, the health display may also include various settings, advice, frequently asked questions, etc. In one embodiment, the health display may be presented on a secure web page accessible by authorized users. In one embodiment, the health display may be a downloadable application, which obtains data from the central SIMS database via a secure connection. Alternative ways of accessing and presenting this data may be used. In one embodiment, the display may be changed depending on the available screen real-estate. In one embodiment, the data may be accessible, in a different form, via smaller devices.

Figure 4:
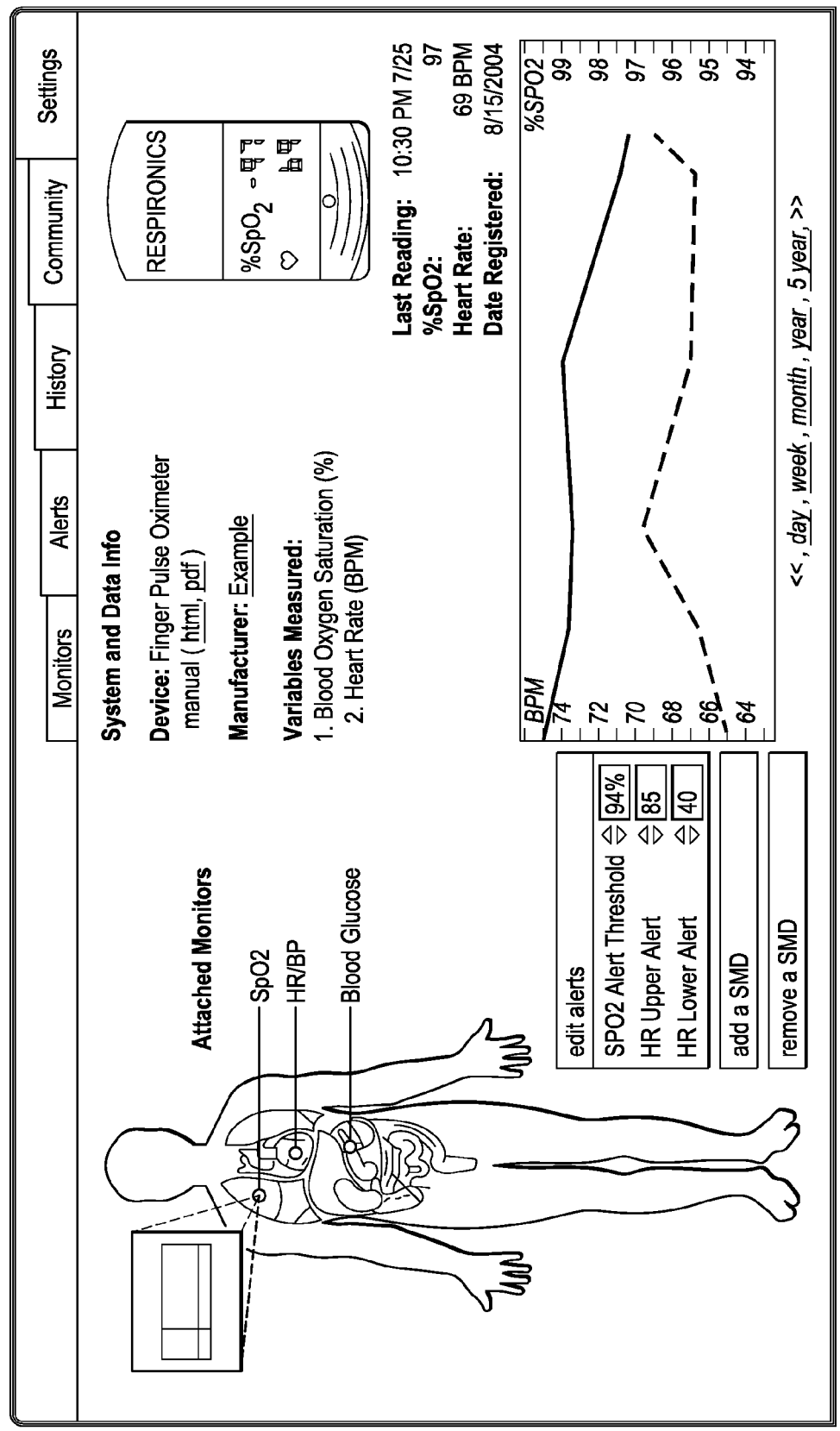
FIG. 4 is an exemplary overview diagram of an individual's health data.

FIG. 4 is an exemplary overview diagram of an individual's health data. On the left hand side 410 an outline of a user can be seen. The outline includes attached monitors and corresponding body-aspects. In one embodiment, the user may mouse over a particular body aspect, and have a pop-up window 430 display basic parameter data associated with that body-part. The user can also click a body-part, and open the frame on the right 420, which displays additional data. In one embodiment, the pop-up window 430 may further list any associated SMDs which have been used to obtain the data.

In one embodiment, alerts 440 associated with the selected device displayed on the right 420, are shown as well. In one embodiment, the alerts 440 may be modified by the user from this list.

In one embodiment, the user may further add or remove SMDs from the listing 450. In one embodiment, as a recognized SMD is selected, the corresponding body-parts are highlighted, and the reference data is added to the outline 420.

On the right hand side 420, a particular selected device and its associated data are shown. As can be seen, the individual's health data shown here is the data from a finger pulse oximeter, which measures blood oxygen saturation and heart rate. The data may include historical readings for the selected device, the last reading, or another method of displaying such data. In one embodiment, the user may set a display preference.

Figure 5:
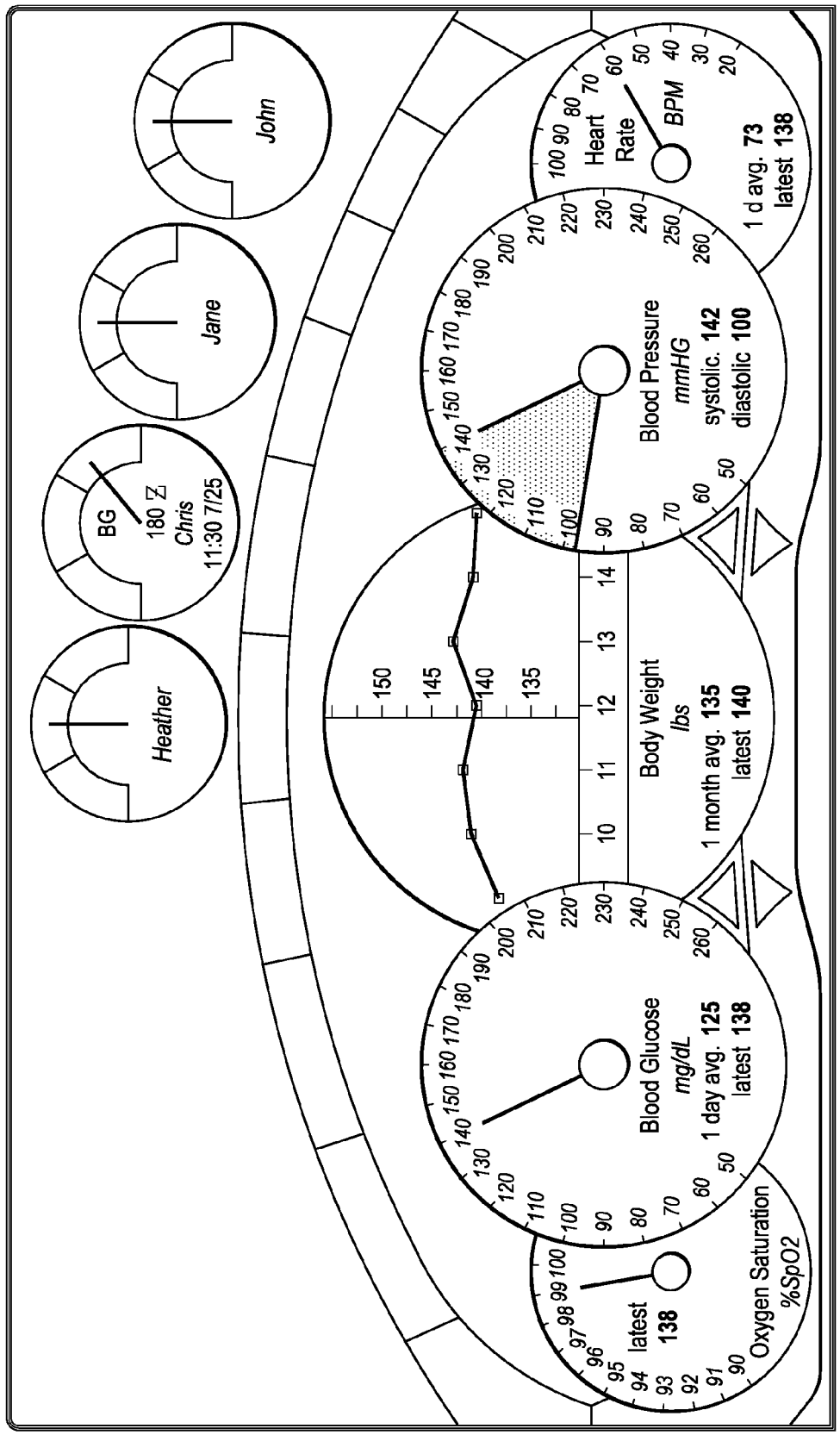
FIG. 5 is an exemplary health dashboard providing a compact view of health data to a user.

FIG. 5 is an exemplary health dashboard providing a compact view of health data to a user. In one embodiment, this is a small application which can show the overall health condition of one or more users. In one embodiment, this small application may be designed to be on a user's desktop. In one embodiment, the application may be implemented in Java, or a similar language. In one embodiment, the application may periodically pull data from the server. Alternatively, the data may be periodically pushed to the application by the server.

The "instant summary" 510 for each person shows a simple dial, which displays an overall health condition ranging from good, through acceptable, and to problem. Of course, more precise or smaller divisions may be displayed.

In one embodiment, this data may be color coded, for example good being green, acceptable being yellow, and problem being red. Alternative methods of indicating ranging from labels to icons and other colors may be used.

As can be seen, the instant summary 510 for three of the four displays here are in the "neutral zone." One instant summary 520 shows a user hovering in the "problem" zone. In that instance, in one embodiment, additional information is displayed. In this instance, the information displayed shows the measurement which is not in the acceptable range. Here, the measurement is blood glucose level (BG) which is at 180. In one embodiment, the display may also show the time the last measurement was taken. In one embodiment, the instant summary 510 concatenates all health parameters received from a user, to generate an "overall" view. In one embodiment, the indicator always shows a "problem" if any one of the health parameters reach an alert level. This may enable a simple display for a health professional, caregiver, or family member who wishes to monitor the health state of many users at the same time.

The user may, in one embodiment, by clicking on one of the instant summaries 510, open the main dashboard 530. The main dashboard in one embodiment similarly uses a dial-type interface to indicate readings. In one embodiment, this interface is designed to resemble a car's gauges, since that is an intuitive way of interacting with a large number of measurements. In one embodiment, the dials may display current measurements, average measurements, or range of measurements.

In one embodiment, from the main dashboard 530, the user may click on any of the dials to receive more in-depth data about the measurements associated with the particular health parameter.

Figure 6B:
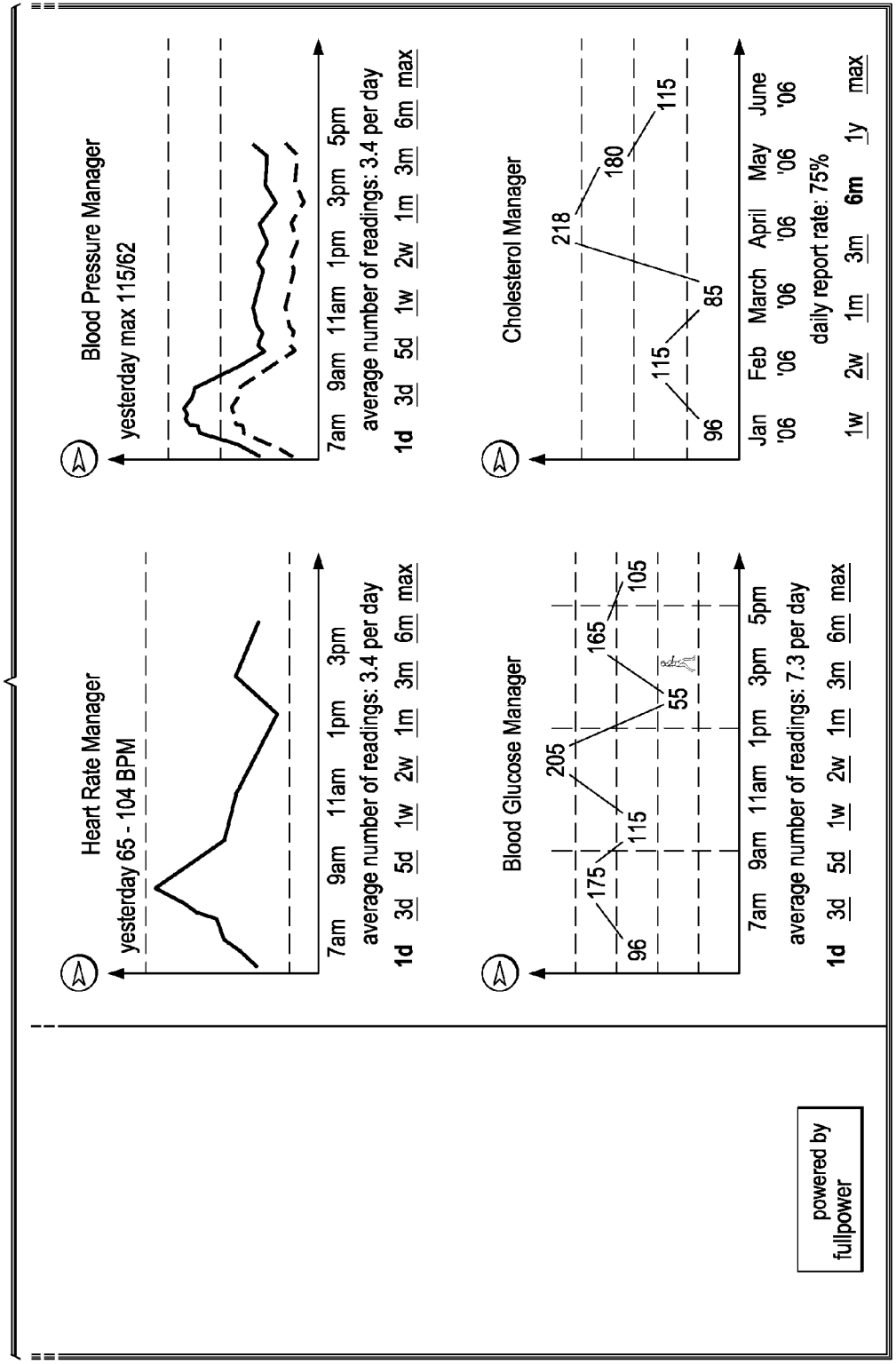
FIG. 6 is an exemplary user interface page, including a summary of data.

FIG. 6 is an exemplary user interface page, including a summary of data. The selected tab 605 shows an overview of the health parameters associated with a particular user. These health parameters may include weight, activity/cardio, heart rate, blood pressure, blood glucose, cholesterol, blood oxygen levels, and various other parameters which may be measured by one or more SMDs. While the particular display shows a set of SMDs, the present system is designed to be able to display results data from any sensor, monitor, or device, whose data may be entered into the SIMS, whether manually or automatically.

In one embodiment, the user may further select any of the individual health parameters 615 to display them in more detail. One embodiment of this user interface feature is described in more detail in U.S. patent application Ser. No. 11/657,199, filed Jan. 23, 2007.

Figure 7:
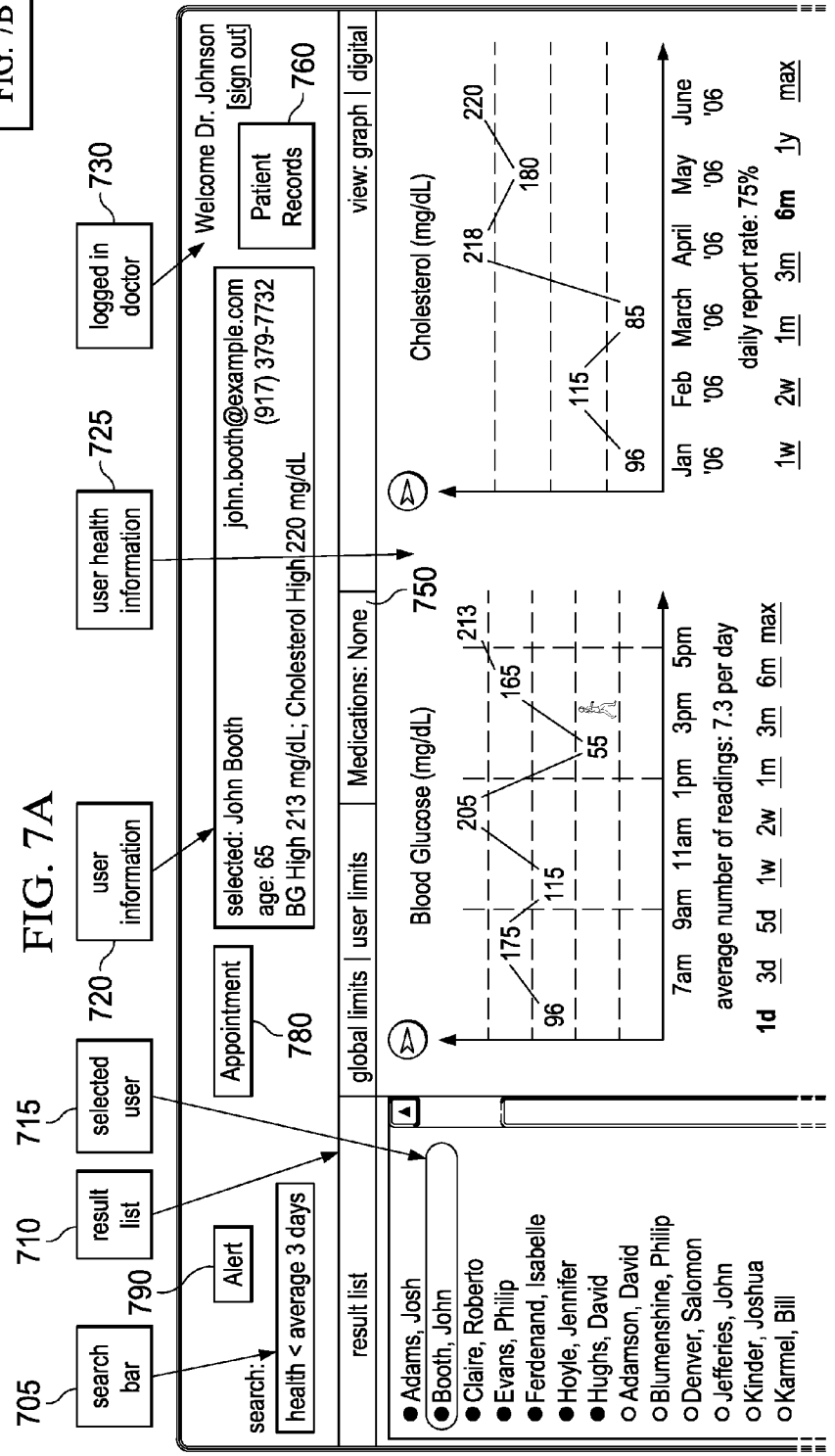
FIG. 7 is an exemplary health data display for a healthcare provider.
Figure 7B:
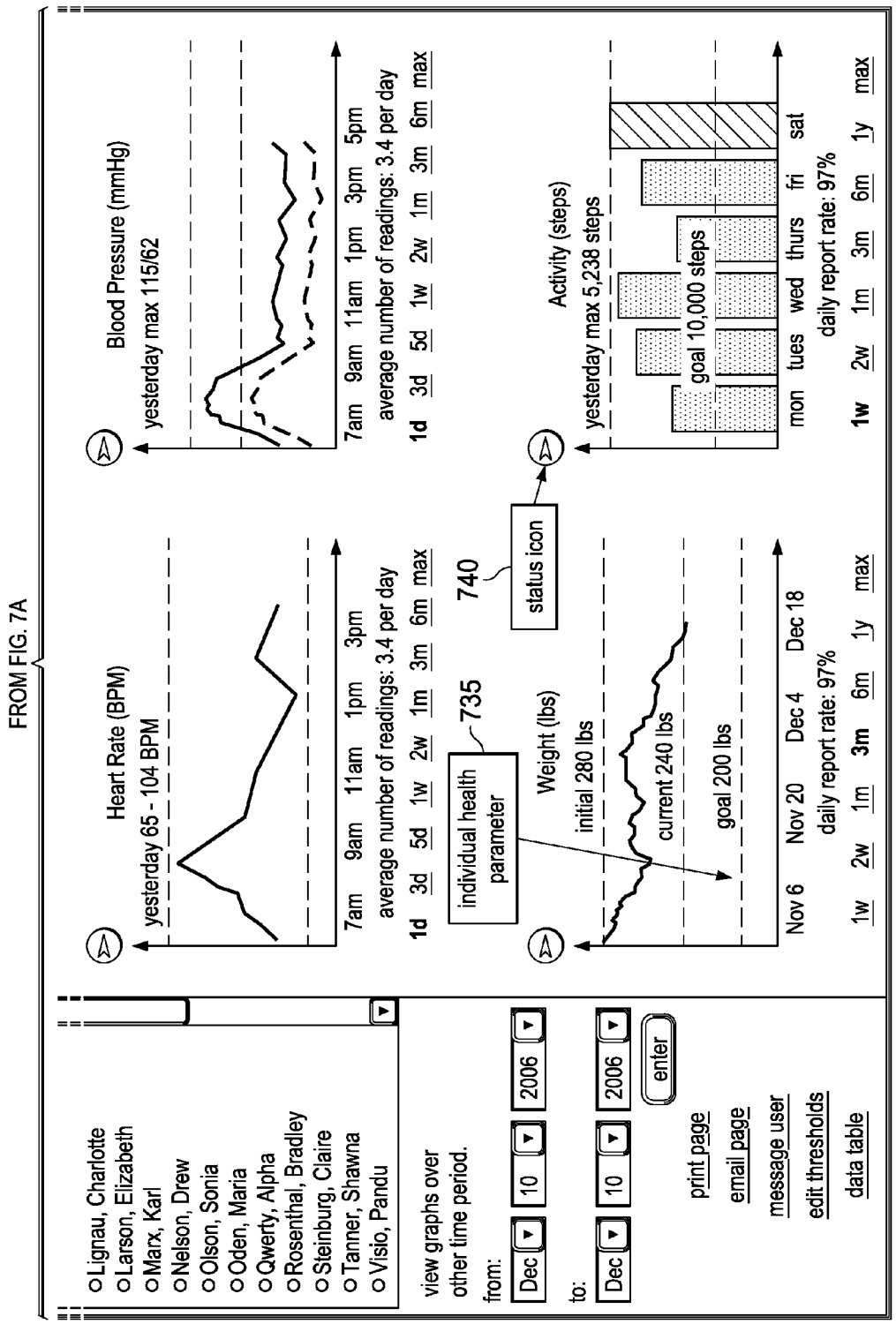

FIG. 7 is an exemplary health data display for a healthcare provider. As can be seen, the healthcare provider can visually see the health parameters of many individuals. The healthcare provider may be a doctor, a nurse, a home care provider, or another individual who is tasked with monitoring the health of multiple individuals.

In one embodiment, the primary interface for the healthcare provider is a results list 710, which displays all of the patients associated with the healthcare provider. In one embodiment, the healthcare provider can search among the users, using search tools 705.

In one embodiment, the particular users whose overall condition is not in the good or acceptable range are highlighted. In one embodiment, only those patients whose condition has changed for the worse are highlighted. In one embodiment, the user can select which users to highlight. In one embodiment, multiple types of highlighting may be done. For example, users whose next scheduled appointment is within a week (or other time period) may be highlighted. Users whose health parameters are problematic, or whose health parameters have changed for the worse may be highlighted. Users whose health parameters have improved, may also be highlighted.

In one embodiment, the search function enables the healthcare provider to also do searches based on any parameters, including scheduled visits, health parameters, changes in health parameters including first derivatives, trends, and any other relevant factors.

In one embodiment, the healthcare provider may select a particular user 715 from the results list 710. The more detailed records of the selected user may be displayed as user health information 725. This may enable the healthcare provider to see all of the relevant self-measured parameters for the patient. In one embodiment, the relevant measurements taken by a doctor, nurse, or other third party are highlighted or otherwise indicated. In one embodiment, if there is a significant discrepancy between self-measured data and third party data, this is highlighted as well. This enables the healthcare provider to visually see trends and easily identify problems.

The user information 720 may also provide additional data. In one embodiment, the user's health chart may also be available in this view. In one embodiment, all of the medications 750 taken by the user, including dosage, are also displayed. In one embodiment, the user's full medical record may be available in this format. In one embodiment, all medical data is stored securely and in compliance with applicable laws.

In one embodiment, the individual health parameters may be adjusted to view a different time span, or view the data in graphical or non-graphical format. For example, in the figure shown, the blood pressure is recorded for one day. An alternative display may provide a month view, with each day having a range-line showing the top & bottom readings.

In one embodiment, there is a simple mechanism for the healthcare provider to send an alert 790 or other notice to the individual user whose data has been received. For example, if the healthcare provider is concerned about something, he or she can send a notification to the user via the alert mechanisms that are part of the SIMS system. In one embodiment, the healthcare provider may select a "severity" for the alert, and the notification mechanism used by the alert may depend on severity. For example, to suggest to the user that a trend needs to be improved, and the user should walk more, a low severity alert indicated by an email may be sufficient. On the other hand, if the health data indicates a severe problem, the alert may be sent via voice message, or may be distributed to multiple parties.

In one embodiment, there is also a simple mechanism for the healthcare provider to schedule an appointment 780 with a user, if the user's medical data triggers the need for such an appointment.

Note that a healthcare provider may be a doctor, an insurance agent, a medical reviewer, or any other professional who legally has access to multiple user's health data in this format. The healthcare provider display is, of course, provided in a secure format, and designed to comply with HIPAA regulations.

Figure 8:
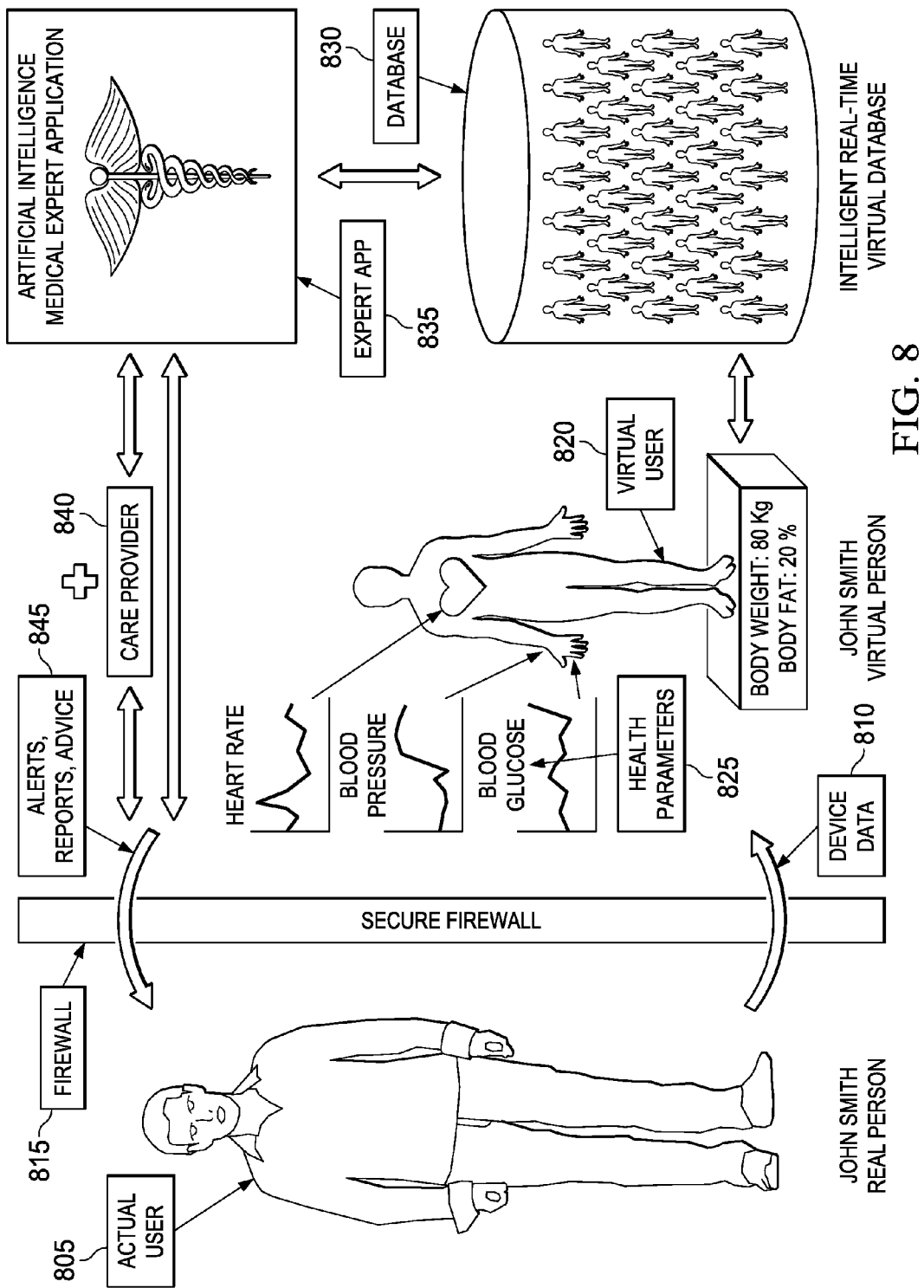
FIG. 8 is an illustration of the relationship between the virtual user and the real user.

FIG. 8 is an illustration of the relationship between the virtual user and the real user. The actual user 805 provides device data 810. Device data 810 may be provided automatically by various SMDs, or entered by the user 805.

The device data 810, in one embodiment is stored as health parameter data 825, in the SIMS database 830. In one embodiment, the SIMS database is behind a secure firewall.

In one embodiment, the SIMS database 830 is only accessible to authorized users. In one embodiment, each user's device data 810 is stored in encrypted form, and only users who are authorized to view the device data 810 can decrypt it.

The virtual user 820 is a construct created by the SIMS system. The virtual user 820 is a way to measure the health status of the actual user 805, and get a snapshot of the overall health data. Health parameters 825 are associated with the virtual user as well.

In one embodiment, the database 830 is a virtual database. In other words, the data is not in a centralized database, but rather distributed in various ways. However, the individual user's virtual person 820 can be called up from the virtual database 830.

In one embodiment, an expert application 835 is used to evaluate the virtual user. The expert application 835 is used to evaluate the user's data. In one embodiment, the expert application 835 analyzes data from the database 830. In one embodiment, whenever new data is added to the database 830, the expert application 835 re-analyzes the complete data. In another embodiment, the database 830, in addition to storing raw device data 810, also stores analysis data. Thus, the expert application 835 uses the new device data 810, and previously stored & calculated analysis data to generate its evaluation.

In one embodiment, the expert application 835 can cause communications with the actual user 810. For example, if the user's health data indicates a problem, an alert 845 may be sent. Furthermore, the user may obtain reports 845, which provide summaries and useful data. In one embodiment, the user may also receive advice. For example, if an incipient problem is detected by expert system 835, instead of an actual alert some advice may be sent. The advice may range from "exercise more" to "drink less coffee in the morning," or similar types of advice. In one embodiment, the actual user 805 may set preferences for the types of advice that will be sent.

In one embodiment, the expert application 835 may also communicate with care provider 840. In one embodiment, care provider 840 may also have access to the raw data in database 830. Care provider 840, in one embodiment, may also be able to generate alerts, reports, and advice 845 for the user.

The "virtual user" 820 enables a care provider, the user, and others to easily obtain current health parameter information, trends, problems, and analysis about a user, without requiring the user to be physically present. This provides a huge advantage since very few users are continuously connected to their health monitors and care providers.

Figure 9:
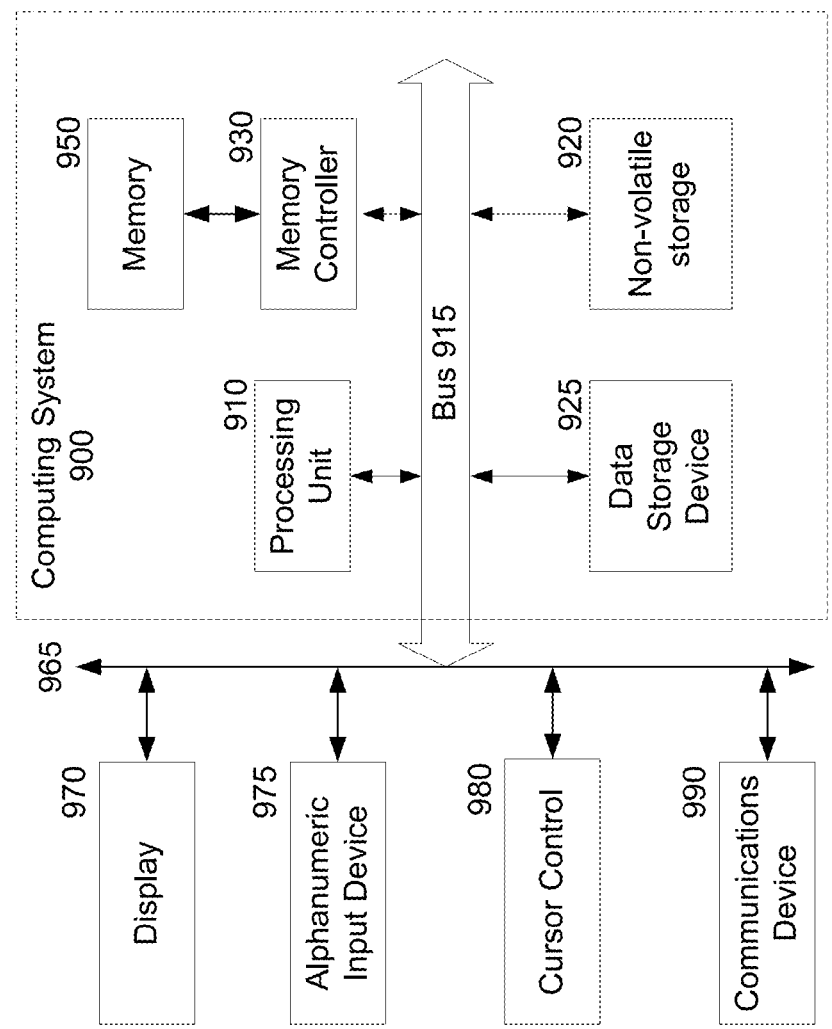
FIG. 9 is one embodiment of a computer system that may be used with the present invention.

FIG. 9 is one embodiment of a computer system that may be used with the present invention. It will be apparent to those of ordinary skill in the art, however that other alternative systems of various system architectures may also be used.

The data processing system illustrated in FIG. 9 includes a bus or other internal communication means 915 for communicating information, and a processor 910 coupled to the bus 915 for processing information. The system further comprises a random access memory (RAM) or other volatile storage device 950 (referred to as memory), coupled to bus 915 for storing information and instructions to be executed by processor 910. Main memory 950 also may be used for storing temporary variables or other intermediate information during execution of instructions by processor 910. The system also comprises a read only memory (ROM) and/or static storage device 920 coupled to bus 915 for storing static information and instructions for processor 910, and a data storage device 925 such as a magnetic disk or optical disk and its corresponding disk drive. Data storage device 925 is coupled to bus 915 for storing information and instructions.

The system may further be coupled to a display device 970, such as a cathode ray tube (CRT) or a liquid crystal display (LCD) coupled to bus 915 through bus 965 for displaying information to a computer user. An alphanumeric input device 975, including alphanumeric and other keys, may also be coupled to bus 915 through bus 965 for communicating information and command selections to processor 910. An additional user input device is cursor control device 980, such as a mouse, a trackball, stylus, or cursor direction keys coupled to bus 915 through bus 965 for communicating direction information and command selections to processor 910, and for controlling cursor movement on display device 970.

Another device, which may optionally be coupled to computer system 900, is a communication device 990 for accessing other nodes of a distributed system via a network. The communication device 990 may include any of a number of commercially available networking peripheral devices such as those used for coupling to an Ethernet, token ring, Internet, or wide area network. The communication device 990 may further be a null-modem connection, a wireless connection mechanism, or any other mechanism that provides connectivity between the computer system 900 and the outside world. Note that any or all of the components of this system illustrated in FIG. 9 and associated hardware may be used in various embodiments of the present invention.

It will be appreciated by those of ordinary skill in the art that any configuration of the system may be used for various purposes according to the particular implementation. The control logic or software implementing the present invention can be stored in main memory 950, mass storage device 925, or other storage medium locally or remotely accessible to processor 910.

It will be apparent to those of ordinary skill in the art that the system, method, and process described herein can be implemented as software stored in main memory 950 or read only memory 920 and executed by processor 910. This control logic or software may also be resident on an article of manufacture comprising a computer readable medium having computer readable program code embodied therein and being readable by the mass storage device 925 and for causing the processor 910 to operate in accordance with the methods and teachings herein.

The present invention may also be embodied in a handheld or portable device containing a subset of the computer hardware components described above. For example, the handheld device may be configured to contain only the bus 915, the processor 910, and memory 950 and/or 925. The present invention may also be embodied in a special purpose appliance including a subset of the computer hardware components described above. For example, the appliance may include a processor 910, a data storage device 925, a bus 915, and memory 950, and only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism.

It will be appreciated by those of ordinary skill in the art that any configuration of the system may be used for various purposes according to the particular implementation. The control logic or software implementing the present invention can be stored on any machine-readable medium locally or remotely accessible to processor 910. A machine-readable medium includes any mechanism for storing or transmitting information in a form readable by a machine (e.g. a computer). For example, a machine readable medium includes read-only memory (ROM), random access memory (RAM), magnetic disk storage media, optical storage media, flash memory devices, electrical, optical, acoustical or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A computer-implemented method comprising:
    receiving, by a server, input to set a plurality of recipients for alerts;
    receiving, by the server, data from a set of one or more sensors measuring health data for an actual user;
    associating, by the server, the received data with a virtual user, wherein the virtual user is a representation used to measure a health status of the actual user;
    transmitting, by the server, the data associated with the virtual user to be displayed to a health care provider in a graphical user interface, wherein the graphical user interface includes a user interface element for the health care provider to generate an alert and select a severity level for the alert;
    receiving, by the server, the alert generated by the health care provider using the user interface element and the severity level selected by the health care provider;
    transmitting, by the server, the alert generated by the health care provider to the actual user when the server determines the severity level for the alert is of a first severity level; and
    transmitting, by the server, the alert to the plurality of recipients when the server determines the severity level for the alert is of a second severity level.

2. The computer-implemented method of claim 1, wherein the virtual user includes data representing an age of the actual user.

3. The computer-implemented method of claim 1, wherein the virtual user includes data representing a weight of the actual user.

4. The computer-implemented method of claim 1, further comprising:
    transmitting, by the server to a user device, a report to be displayed on the user device, the report including physical activity of the actual user over a plurality of days.

5. The computer-implemented method of claim 4, wherein the report further includes a daily goal for the physical activity.

6. A non-transitory computer-readable medium storing instructions, which when executed by a processing device within a server, cause the processing device to perform a method comprising:
    receiving, by a server, input to set a plurality of recipients for alerts;
    receiving, by the server, data from a set of one or more sensors measuring health data for an actual user;
    associating, by the server, the received data with a virtual user, wherein the virtual user is a representation used to measure a health status of the actual user;
    transmitting, by the server, the data associated with the virtual user to be displayed to a health care provider in a graphical user interface, wherein the graphical user interface includes a user interface element for the health care provider to generate an alert and select a severity level for the alert;
    receiving, by the server, the alert generated by the health care provider using the user interface element and the severity level selected by the health care provider;
    transmitting, by the server, the alert generated by the health care provider to the user when the server determines the severity level for the alert is of a first severity level; and
    transmitting, by the server, the alert to the plurality of recipients when the server determines the severity level for the alert is of a second severity level.

7. The non-transitory computer-readable medium of claim 6, wherein the virtual user includes data representing an age of the actual user.

8. The non-transitory computer-readable medium of claim 6, wherein the virtual user includes data representing a weight of the actual user.

9. The non-transitory computer-readable medium of claim 6, the method further comprising:
    transmitting, by the server to a user device, a report to be displayed on the user device, the report including physical activity of the actual user over a plurality of days.

10. The non-transitory computer-readable medium of claim 9, wherein the report further includes a daily goal for the physical activity.

11. A computer server comprising:
    a processing device; and
    a memory coupled to the processing device, wherein the memory stores instructions which, when executed by the processing device, cause the computer server to:
        receive input to set a plurality of recipients for alerts;
        receive data from a set of one or more sensors measuring health data for an actual user;
        associate the received data with a virtual user, wherein the virtual user is a representation used to measure a health status of the actual user;
        transmit the data associated with the virtual user to be displayed to a health care provider in a graphical user interface, wherein the graphical user interface includes a user interface element for the health care provider to generate an alert and select a severity level for the alert;
        receive the alert generated by the health care provider using the user interface element and the severity level selected by the health care provider;
        transmit the alert generated by the health care provider to the user when the server determines the severity level for the alert is of a first severity level; and
        transmit the alert to the plurality of recipients when the server determines the severity level for the alert is of a second severity level.

12. The computer server of claim 11, wherein the virtual user includes data representing an age of the actual user.

13. The computer server of claim 11, wherein the virtual user includes data representing a weight of the actual user.

14. The computer server of claim 11, wherein execution of the instructions further cause the computer server to:

transmit, to a user device, a report to be displayed on the user device, the report including physical activity of the actual user over a plurality of days.

\* \* \* \* \*